United States Patent [19]

Togashi et al.

[11] Patent Number: 4,835,240

[45] Date of Patent: May 30, 1989

[54] EPOXY RESIN COMPOSITION

[75] Inventors: Eiki Togashi; Toshimasa Takata, both of Ichihara, Japan

[73] Assignee: Mitsui Petrochemical Industries, Ltd., Tokyo, Japan

[21] Appl. No.: 199,685

[22] Filed: May 31, 1988

[30] Foreign Application Priority Data

May 30, 1987 [JP] Japan .................. 62-133518

[51] Int. Cl.$^4$ ............................ C08G 59/00
[52] U.S. Cl. .................... 528/98; 528/104; 528/106; 528/129; 528/155; 528/230; 525/481; 525/489; 525/534; 525/930; 252/500; 252/511
[58] Field of Search ............... 528/98, 104, 106, 129, 528/155, 230; 525/481, 489, 534, 930; 252/500, 511

[56] References Cited

U.S. PATENT DOCUMENTS

| | | | |
|---|---|---|---|
| 3,941,850 | 3/1976 | Brindell et al. | 568/720 |
| 4,216,298 | 8/1980 | Schreckenberg et al. | 525/439 |
| 4,390,664 | 6/1983 | Kanayama | 525/117 |
| 4,505,844 | 3/1985 | Denisevich, Jr. | 252/500 |
| 4,558,116 | 12/1985 | Wernli et al. | 528/95 |
| 4,663,400 | 5/1987 | Wang et al. | 525/481 |
| 4,690,998 | 9/1987 | Wahle et al. | 528/96 |
| 4,731,423 | 3/1988 | Mendoza et al. | 525/480 |
| 4,759,978 | 7/1988 | Takata | 428/290 |

Primary Examiner—John Kight
Assistant Examiner—S. A. Acquah
Attorney, Agent, or Firm—Sherman and Shalloway

[57] ABSTRACT

An epoxy resin composition comprising a trifunctional epoxy resin derived from a trisphenol having the structure represented by the following general formula

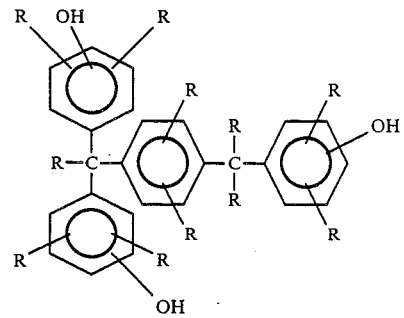

wherein R represents a hydrogen atom, an alkyl group or a halogen atom, and a novolak-type phenolic resin. This epoxy resin composition gives a cured product having excellent pliability and a high glass transition temperature. It is especially useful as a semiconductor encapsulating material.

8 Claims, No Drawings

EPOXY RESIN COMPOSITION

BACKGROUND OF THE INVENTION (1) Field of the Invention

This invention relates to an epoxy resin composition, and more specifically, to an epoxy resin composition capable of giving a cured product having excellent pliability and a high glass transition temperature.

(2) Description of the Prior Art

Epoxy resin molding materials of the type in which an epoxy resin is cured by using a novolak-type phenolic resin are much used as, for example, a semiconductor encapsulating material since they are excellent in adhesiveness and moisture resistance. In the molding materials of this type, however, internal stresses occur owing to shrinkage during molding and curing. This leads to the disadvantage that as the chip size increases, cracks are formed in the resin or chips, and bonding wires undergo breakage.

It is known that as means for solving this problem, a flexibilizing agent such as silicone resins or polybutadiene is incorporated in the molding materials so as to lower the modulus of the encapsulating resin (to make it pliable). However, in this method, the glass transition temperature of the cured resin abruptly decreases, and its electrical characteristics in a high temperature region are degraded. It is difficult therefore to obtain molded products having high reliability. Another defect is that the mechanical strength of the cured product is reduced.

SUMMARY OF THE INVENTION

It is an object of this invention therefore to provide an epoxy resin composition capable of giving a cured product having pliability (low modulus) and a high glass transition temperature.

The present invention provides an epoxy resin composition comprising as essential components (A) a trifunctional epoxy compound obtained by condensation reaction of a phenol derivative represented by the following general formula

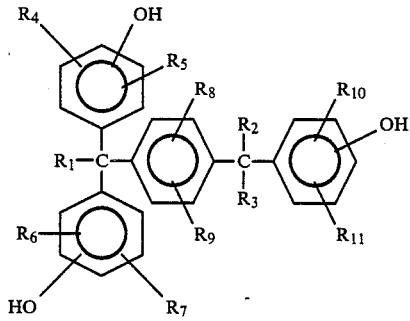

(I)

wherein $R_1$ to $R_3$ represents a hydrogen atom or an alkyl group having not more than 6 carbon atoms, $R_4$ to $R_{11}$ represent a hydrogen atom, an alkyl group having not more than 6 carbon atoms or a halogen atom, and the groups $R_1$ to $R_{11}$ may be identical with each other, with epichlorohydrin, and (B) a novolak-type phenolic resin.

The important feature of the present invention lies in the use of a specific trifunctional epoxy resin obtained from the phenol derivative of the above general formula. By combining this trifunctional epoxy resin with the novolak-type phenolic resin, it is possible to lower the modulus of the cured product (make it pliable) and increase the glass transition temperature. This also effectively inhibit the reduction of its strength.

The novolak-type phenolic resin used as component (B) in the epoxy resin composition of this invention serves as a curing agent.

DETAILED DESCRIPTION OF THE PREFERRED EMBODIMENTS (A) Epoxy resin

The epoxy resin used in this invention can be produced by etherifying a trisphenol represented by general formula (I)

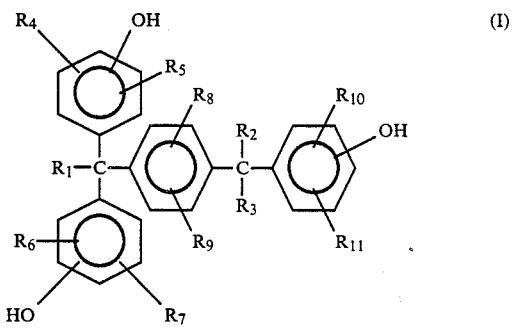

(I)

wherein $R_1$ to $R_3$ represents a hydrogen atom or an alkyl group having not more than 6 carbon atoms, $R_4$ to $R_{11}$ represent a hydrogen atom, an alkyl group having not more than 6 carbon atoms or a halogen atom, and the groups $R_1$ to $R_{11}$ may be identical with each other, with epichlorohydrin in the presence of a suitable etherification catalyst and then dehydrohalogenating the product.

The trisphenol of general formula (I) is obtained by reacting an aromatic ketone or aldehyde having at the side chain an aliphatic group with an ethylenic double bond, with a monohydric phenol.

When isopropenyl acetophenone, for example, is used as the aromatic ketone, a trisphenol is obtained in accordance with the following reaction scheme.

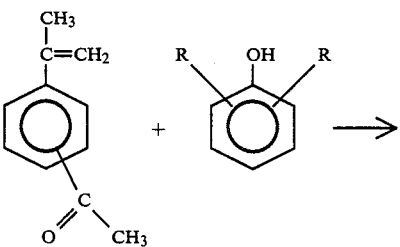

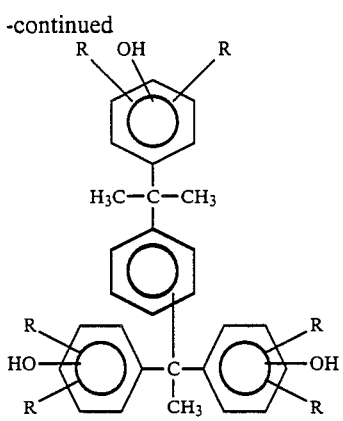

It is seen from this reaction scheme that the types of the groups $R_1$ to $R_3$, $R_8$ and $R_9$ are determined depending upon the type of the aromatic ketone or aldehyde used, and the types of the groups $R_4$ to $R_7$, $R_{10}$ and $R_{11}$ are determined depending upon the type of the monohydric phenol used. For example, when an aromatic aldehyde is used, $R_1$ in general formula (I) is a hydrogen atom.

A compound of general formula (I) in which all aromatic rings having a phenolic hydroxyl group are identical may be obtained by carrying out the above reaction using the corresponding phenol. A compound of general formula (I) in which all aromatic rings having a phenolic hydroxyl group are different may be obtained by carrying out the reaction using a mixture of the corresponding phenols.

A trisphenol of general formula (I) having halogen atoms at the side chains of the aromatic rings may be produced by performing the above reaction using a halogen-substituted monohydric phenol. If desired, it may be obtained by first producing a trisphenol and then halogenating it.

The reaction of the aromatic ketone or aldehyde with the monohydric phenol may be carried out, for example, by using a protonic acid such as hydrochloric acid as a catalyst and adding the aromatic ketone or aldehyde dropwise to a mixture of a stoicheometrically excessive amount of the monohydric phenol and the catalyst. As required, methylmercaptan or mercaptoacetic acid, for example, may be added to the reaction system as a promotor. This reaction is carried out usually at a temperature of 40° to 80° C. under atmospheric or elevated pressure.

The trifunctional epoxy resin used in this invention is obtained by etherifying the trisphenol with epichlorohydrin and then dehydrohalogenating the product. This reaction itself may be carried out by a known method. For example, the etherification may be carried out in the presence of about 0.005 to 5 mole %, per equivalent of the phenolic hydroxyl groups of the trisphenol, of an etherification catalyst, for example, a tertiary amine such as trimethylamine or triethylamine, a tertiary phosphine such as triphenylphosphine or tributylphosphine, a quaternary ammonium salt such as tetramethyl ammonium chloride, tetramethyl ammonium bromide, tetraethyl ammonium chloride, tetraethyl ammonium bromide or choline chloride, a quaternary phosphonium salt such as tetramethylphsphonium bromide, tetramethylphosphonium iodide or triphenylpropylphosphonium bromide or a tertiary sulfonium salt such as benzyldibutylsulfonium chloride or benzyldimethylsulfonium chloride, preferably in the presence of the quaternary ammonium salt.

The etherification step is carried out until at least 50%, preferably at least 80%, of the hydroxyl groups of the trisphenol are etherified. The reaction is carried out generally at a temperature of about 60° to 110° C. for about 1 to 12 hours. Preferably, water should not be present at this time. If water is present, its amount is adjusted to not more than 3.0% by weight.

The etherification reaction product still containing the unreacted epihalohydrin is submitted to the next dehydrohalogenating step. This reaction is carried out by using at least 0.5 mole, especially at least 0.8 mole, per equivalent of the phenolic hydroxyl groups of the trisphenol, of a catalyst, for example an alkali metal hydroxide such as sodium hydroxide, potassium hydroxide or lithium hydroxide, preferably sodium hydroxide. To avoid troubles such as gellation, the amount of the alkali metal compound as the catalyst is preferably limited to not more than 1 mole.

After the reaction, the reaction mixture is distilled under reduced pressure to remove the unreacted epichlorohydrin and washed with water, for example, to remove the by-product salt, and as required neutralized with a weak acid such as phosphoric acid or sodium dihydrogen phosphate. Subsequent drying gives the desired epoxy resin.

As can be seen from the structure of the trisphenol of general formula (I), the trifunctional epoxy resin used in this invention is characterized by the chemical structure in which the four benzene rings are linked in branches via one carbon atom. It has an epoxy equivalent of 198 to 400 and a softening point of 50° to 120° C.

Specific examples of this epoxy resin include
1-(α-methyl-α-(4'-glycidoxyphenyl)ethyl)-4-(α',α'-bis(-4''-glycidoxyphenyl)ethyl)benzene,
1-(α-methyl-α-(2'-methyl-4'-glycidoxy-5'-tert.butylphenyl)ethyl)-4-(α',α'-bis(2''-methyl-4''-glycidoxy-5''-tert.butylphenyl)ethyl)benzene,
1-(α-methyl-α-(3',5'-dimethyl-4'-glycidoxyphenyl)ethyl)-4-(α',α'-bis(3'',5''-dimethyl-4''-glycidoxyphenyl)ethyl)benzene,
1-(α-methyl-α-(3'-tert.butyl-4'-glycidoxyphenyl)ethyl)-4-(α',α'-bis(3''-tert.butyl-4''-glycidoxyphenyl)ethyl)benzene,
1-(α-methyl-α-(3'-methyl-4'-glycidoxy-5'-tert.butylphenyl)ethyl)-4-(α',α'-bis(3''-methyl-4''-glycidoxy-5''-tert.butylphenyl)ethyl)benzene, and
1-(α-methyl-α-(2',5'-dimethyl-4'-glycidoxyphenyl)ethyl)-4-(α',α'-bis(2'',5''-dimethyl-4''-glycidoxyphenyl)ethyl)benzene.

In the trifunctional epoxy resin, each of the phenolic hydroxyl groups in formula (I) is preferably bonded to the para-position of the phenyl group. Preferably, each of $R_1$ to $R_4$ is an alkyl group having not more than 4 carbon atoms, especially a methyl group, and each of $R_4$ to $R_9$ is a hydrogen atom, a methyl group or a tertiary butyl group.

Another epoxy resin such as an o-cresol novolak-type epoxy resin may be used jointly so long as it does not impair the purpose of this invention. It may be used, for example, in an amount of at least 5 parts by weight, especially at least 10 parts by weight, per 100 parts by weight of the trifunctional epoxy resin.

(B) Novolak-type phenolic resin

In the present invention, a novolak-type phenolic resin is used as a curing agent for the trifunctional epoxy resin (A).

The phenolic resin is obtained by condensing phenol or an alkyl-substituted phenol such as o-cresol, p-cresol, t-butylphenol, cumylphenol or nonylphenol with formaldehyde in an acid catalyst. Those having a hydroxyl equivalent of 100 to 150 and a softening point of 60° to 110° C. are preferably used.

The phenolic resin is incorporated in an amount of 20 to 120 parts by weight, especially 40 to 100 parts by weight, per 100 parts by weight of the trifunctional epoxy resin (A).

Additives

The epoxy resin composition of this invention comprises the trifunctional epoxy resin and the novolak-type phenolic resin described above as essential components. It may contain known additives such as a curing promoter, a filler, a mold releasing agent, a coloring agent, a flame retardant, and a coupling agent.

Examples of the curing promoter are imidazoles such as 2-methyl-4-methylimidazole, 2-phenylimidazole and 2-ethyl-4-methylimidazoleazine, hydrazide compounds such as dibasic acid hydrazide and a boron trifluoride-amine complex compound. The curing promoter may be used in an amount of 0.1 to 20 parts by weight per 100 parts by weight of the trifunctional epoxy resin.

Examples of the filler are silica, alumina, talc, mica, heavy calcium carbonate, kaolin, diatomaceous earth, asbestos, graphite, boron, silicon carbide, carbon fibers and glass fibers. The filler may be used in an amount of 50 to 900 parts by weight per 100 parts by weight of the components (A) and (B) combined.

Examples of the mold releasing agent are carnauba wax, montan wax, ester wax, stearic acid, calcium stearate, zinc stearate, 12-hydroxystearic acid and calcium 12-hydroxystearate. The mold releasing agent may be used in an amount of 0.1 to 10 parts by weight per 100 parts by weight of the components (A) and (B) combined.

Carbon black is an example of the coloring agent. It may be used in an amount of 0.01 to 5 parts by weight per 100 parts by weight of the components (A) and (B) combined.

Halogenated polyphenols such as tetrabromobisphenol A and antimony oxide may, for example, be used as the flame retardant. The flame retardant may be used in an amount of 12 to 25 part by weight per 100 parts by weight of the components (A) and (B) combined.

Silane compounds such as γ-glycidoxypropyl-trimethoxysilane may, for example, be used as the coupling agent. It may be used in an amount of 0.1 to 10 parts by weight per 100 parts by weight of the components (A) and (B) combined.

Resin composition

The resin composition of this invention may be prepared usually by kneading the above components at a temperature of about 80° to 120° C. by using a twin-screw extruder or a roll mill such as a two-roll mill.

The resulting epoxy resin of the composition may be cooled and pulverized after kneading, and used as various molding materials.

As shown in the following examples, cured molded articles having a low modulus, a high glass transition temperature and excellent mechanical properties such as high strength can be obtained. Thus, molded products having high reliability can be obtained from the epoxy resin composition of this invention.

Since the occurrence of internal stresses owing to shrinkage during curing is suppressed, the epoxy resin composition of this invention is especially useful as a semiconductor encapsulating material.

The following examples illustrate the present invention more specifically. All parts in these examples are by weight.

EXAMPLE 1

The components in accordance with the following compounding recipe were kneaded by two rolls at 100° C. for 5 minutes, cooled, and pulverized to obtain a molding material.

| Compounding recipe | |
|---|---|
| 1-(α-methyl-α(4'-glycidoxy-phenyl)ethyl)-4-(α',α'-bis-(4''-glycidoxyphenylethyl)benzene (epoxy equivalent 269) | 100 parts |
| Novolak-type phenolic resin (softening point 97° C.) | 38 parts |
| 2-Ethyl-4-methylimidazoleazine (curing promoter) | 2 parts |
| Amorphous silica | 495 parts |
| Carbon black | 1 part |
| Silane coupling agent (KBM-403, produced by Shin-etsu Chemical Co., Ltd.) | 2.5 parts |
| Carnauba wax | 2 parts |

The resulting molding material was molded at 160° C. and 70 kg/cm² for 5 minutes by a transfer molding machine to form a sheet having a thickness of 4 mm.

The sheet was then post-cured at 160° C. for 8 hours to prepare test pieces in accordance with JIS K-6911, and its flexural strength, flexural moduluis and glass transition temperature were measured on these test pieces in accordance with JIS K-6911. The results are shown in Table 1.

EXAMPLE 2

A molding material was prepared in the same way as in Example 1 except that the following compounding recipe was used. The various properties were measured as in Example 1, and the results are shown in Table 1.

| Compounding recipe | |
|---|---|
| 1-(α-methyl-α(4'-glycidoxy-phenyl)ethyl)-4-(α',α'-bis-(4''-glycidoxyphenyl)ethyl)benzene (epoxy equivalent 269) | 50 parts |
| o-Cresol novolak-type epoxy resin (epoxy equivalent 215) | 50 parts |
| Novolak-type phenol (softening point 97° C.) | 43 parts |

EXAMPLE 3

A molding material was prepared in the same way as in Example 1 except that the following compounding recipe was used. The various properties were measured as in Example 1, and the results are shown in Table 1.

| Compounding recipe | |
|---|---|
| 1-(α-methyl-α(4'-glycidoxy-phenyl)ethyl)-4-(α',α'-bis-(4''-glycidoxyphenyl)ethyl)benzene (epoxy equivalent 269) | 30 parts |
| o-Cresol novolak-type epoxy | 70 parts |

| Compounding recipe | |
|---|---|
| resin (epoxy equivalent 215) | |
| Novolak-type phenol (softening point 97° C.) | 47 parts |

COMPARATIVE EXAMPLE 1

A molding material was prepared in the same way as in Example 1 except that the following compounding recipe was used. The various properties were measured as in Example 1, and the results are shown in Table 1.

| Compounding recipe | |
|---|---|
| o-Cresol novolak-type epoxy resin (epoxy equivalent 215) | 100 parts |
| Novolak-type phenolic resin (softening point 97° C.) | 45 parts |
| 2-Ethyl-4-methylimidazoleazine | 2 parts |
| Amorphous silica | 495 parts |
| Carbon black | 1 part |
| Silane coupling agent (KBM-403, produced by Shin-etsu Chemical Co., Ltd.) | 2.5 parts |
| Carnauba wax | 2 parts |

COMPARATIVE EXAMPLE 2

A molding material was prepared in the same way as in Comparative Example 1 except that 8.6 parts of carboxyl-terminated polybutadiene rubber (HYCAR CTB 2000X162, a product of Ube Industries, Ltd.) was added further. The properties of the molding material were measured as in Example 1, and the results are shown in Table 1,

COMPARATIVE EXAMPLE 3

A molding material was prepared in the same way as in Comparative Example 1 except that 8.6 parts of carboxyl-terminated polybutadiene acrylonitrile rubber (HYCAR CTBN 1300X8, a product of Ube Industries, Ltd.) was added further. The properties of the molding material were measured as in Example 1, and the results are shown in Table 1.

It is understood from the results of the above Examples and Comparative Examples that when an attempt is made to lower the modulus of a cured molded article by adding a rubber component to the epoxy resin, both its strength and glass transition temperature are decreased, but that when the specific trifunctional epoxy resin is used in accordance with this invention, the decrease of the strength and the glass transition temperature is effectively suppressed.

TABLE 1

| | Ex. 1 | Ex. 2 | Ex. 3 | CEx. 1 | CEx. 2 | CEx. 3 |
|---|---|---|---|---|---|---|
| Flexural strength (kg/mm$^2$) | 14 | 14 | 13.5 | 12 | 11.5 | 11 |
| Flexural modulus (kg/mm$^2$) | 1350 | 1400 | 1450 | 1650 | 1350 | 1400 |
| Glass transition temperature (°C.) | 168 | 168 | 168 | 168 | 160 | 160 |

Ex. = Example
CEx. = Comparative Example

What we claim is:

1. An epoxy resin composition comprising as essential components
   (A) a trifunctional epoxy compound obtained by condensation reaction of a phenol derivative represented by the following general formula

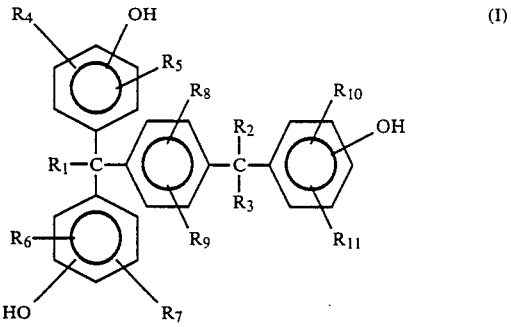

wherein $R_1$ to $R_3$ represents a hydrogen atom or an alkyl group having not more than 6 carbon atoms, $R_4$ to $R_{11}$ represents a hydrogen atom, an alkyl group having not more than 6 carbon atoms or a halogen atom, and the groups $R_1$ to $R_{11}$ may be identical with each other, with epichlorohydrin, and
   (B) a novolak-type phenolic resin.

2. The composition of claim 1 wherein the amount of the novolak-type phenolic resin is 20 to 120 parts by weight per 100 parts by weight of the epoxy resin.

3. The composition of claim 1 wherein in general formula (I), the three phenolic hydroxyl groups are each bonded to the para-position of the phenol group.

4. The composition of claim 1 wherein in general formula (I), each of $R_1$ to $R_4$ represents an alkyl group having not more than 4 carbon atoms.

5. The composition of claim 4 wherein in general formula (I), each of $R_1$ to $R_4$ represents a methyl group.

6. The resin composition of claim 1 wherein in general formula (I), each of $R_4$ to $R_{11}$ represents a hydrogen atom, a methyl group or a tertiary butyl group.

7. The composition of claim 1 wherein the trifunctional epoxy resin is selected from the group consisting of
   1-(α-methyl-α-(4'-glycidoxyphenyl)ethyl)-4-(α',α'-bis(4"-glycidoxyphenyl)ethyl)benzene,
   1-(α-methyl-α-(2'-methyl-4'-glycidoxy-5'-tert.butylphenyl)ethyl)-4-(α',α'-bis(2"-methyl-4"-glycidoxy-5"-tert.butylphenyl)ethyl)benzene,
   1-(α-methyl-α-(3',5'-dimethyl-4'-glycidoxyphenyl)ethyl)-4-(α',α'-bis(3",5"-dimethyl-4"-glycidoxyphenyl)ethyl)benzene,
   1-(α-methyl-α-(3'-tert.butyl-4'-glycidoxy-phenyl)ethyl)-4-(α',α'-bis(3"-tert.butyl-4"-glycidoxyphenyl)ethyl)benzene,
   1-(α-methyl-α-(3'-methyl-4'-glycidoxy-5'-tert.butylphenyl)ethyl)-4-(α',α'-bis(3"-methyl-4"-glycidoxy-5"-tert.butylphenyl)ethyl)benzene, and
   1-(α-methyl-α-(2',5'-dimethyl-4'-glycidoxyphenyl)ethyl)-4-(α',α'-bis(2",5"-dimethyl-4"-glycidoxyphenyl)ethyl)benzene.

8. A semiconductor encapsulating material composed of the epoxy resin composition of claim 1.

* * * * *